(12) United States Patent
Jones et al.

(10) Patent No.: US 9,649,454 B2
(45) Date of Patent: May 16, 2017

(54) DELIVERY DEVICE AND RELATED METHODS

(71) Applicant: Manta Devices, LLC, Roslindale, MA (US)

(72) Inventors: Andrew Jones, Roslindale, MA (US); Richard L. Miller, Needham, MA (US)

(73) Assignee: Manta Devices, LLC, Cambridge, MA (US)

( * ) Notice: Subject to any disclaimer, the term of this patent is extended or adjusted under 35 U.S.C. 154(b) by 275 days.

(21) Appl. No.: 13/886,322

(22) Filed: May 3, 2013

(65) Prior Publication Data

US 2013/0291865 A1    Nov. 7, 2013

Related U.S. Application Data

(60) Provisional application No. 61/641,993, filed on May 3, 2012.

(51) Int. Cl.
*A61M 15/00* (2006.01)

(52) U.S. Cl.
CPC ........ *A61M 15/00* (2013.01); *A61M 15/0021* (2014.02); *A61M 15/0028* (2013.01);
(Continued)

(58) Field of Classification Search
CPC .......... A61M 15/0008; A61M 15/0028; A61M 15/0031; A61M 15/0033; A61M 15/0036;
(Continued)

(56) References Cited

U.S. PATENT DOCUMENTS

| | | |
|---|---|---|
| 2,307,986 A | 1/1943 | Bolte et al. |
| 2,860,638 A | 11/1958 | Bartolomeo |

(Continued)

FOREIGN PATENT DOCUMENTS

| | | |
|---|---|---|
| DE | 4400083 A1 | 7/1995 |
| EP | 0407276 | 1/1991 |

(Continued)

OTHER PUBLICATIONS

Partial International Search Report from related International Application No. PCT/US2008/008303 dated Dec. 4, 2008.

(Continued)

*Primary Examiner* — Lynne Anderson
*Assistant Examiner* — Elliot S Ruddie
(74) *Attorney, Agent, or Firm* — Grossman Tucker Perreault & Pfleger, PLLC

(57) ABSTRACT

A dose delivery device includes a mouthpiece having an inlet and an outlet, a dose to be delivered to a subject via the mouthpiece and a housing surrounding the mouthpiece and the dose. The mouthpiece or other portion of the device may be moveable to form an opening in the housing, open a dose chamber and/or to extend the mouthpiece from the housing for delivery of the dose. The mouthpiece and housing may be arranged so that the mouthpiece remains attached to the housing after the opening is formed and the mouthpiece is extended from the housing. The housing may include a layer of barrier material that interacts with the mouthpiece to form the opening, e.g., the mouthpiece and barrier material may be moved relative to each other so that the barrier material is pierced. A dose chamber may be formed by a portion of the housing, a portion of the mouthpiece, and/or by any other suitable component of the delivery device. The dose chamber may be enclosed by the housing, and the dose chamber may be open to other spaces in the housing, or may be closed relative to other spaces enclosed by the housing.

18 Claims, 6 Drawing Sheets

(52) U.S. Cl.
CPC .... *A61M 15/0036* (2014.02); *A61M 15/0045* (2013.01); *A61M 2202/064* (2013.01)

(58) Field of Classification Search
CPC .......... A61M 15/0043; A61M 15/0045; A61M 15/0048; A61M 15/0086; A61M 15/0091; A61M 2202/0064
USPC ............ 128/203.12, 203.15, 203.21, 203.23; 604/58
See application file for complete search history.

(56) References Cited

U.S. PATENT DOCUMENTS

| | | |
|---|---|---|
| 2,974,787 A | 3/1961 | Cooper |
| 3,888,253 A | 6/1975 | Watt et al. |
| 2,893,392 A | 6/1976 | Gerstel et al. |
| 4,249,526 A | 2/1981 | Dean et al. |
| 4,338,931 A | 7/1982 | Cavazza |
| 4,601,896 A | 7/1986 | Nugent |
| 5,035,237 A | 7/1991 | Newell et al. |
| 5,167,242 A | 12/1992 | Turner et al. |
| 5,239,993 A | 8/1993 | Evans |
| 5,320,714 A | 6/1994 | Brendel |
| 5,388,572 A | 2/1995 | Mulhauser et al. |
| 5,400,808 A | 3/1995 | Turner et al. |
| 5,476,093 A | 12/1995 | Lankinen |
| 5,501,236 A | 3/1996 | Hill et al. |
| 5,562,918 A | 10/1996 | Stimpson |
| 5,596,982 A | 1/1997 | Blaha-Schnabel |
| 5,622,166 A | 4/1997 | Eisele et al. |
| 5,647,349 A | 7/1997 | Ohki et al. |
| 5,669,378 A | 9/1997 | Pera et al. |
| 5,673,793 A | 10/1997 | Seidler |
| 5,775,320 A | 7/1998 | Patton et al. |
| 5,893,452 A | 4/1999 | De Nervo |
| 5,921,237 A | 7/1999 | Eisele et al. |
| 5,947,117 A | 9/1999 | Herold |
| 5,954,204 A | 9/1999 | Grabowski |
| 6,029,663 A | 2/2000 | Eisele et al. |
| 6,089,228 A | 7/2000 | Smith et al. |
| 6,209,538 B1 | 4/2001 | Casper et al. |
| 6,230,707 B1 | 5/2001 | Horlin |
| 6,234,169 B1 | 5/2001 | Bulbrook et al. |
| 6,328,034 B1 | 12/2001 | Eisele et al. |
| 6,347,629 B1 | 2/2002 | Braithwaite |
| 6,401,712 B1 | 6/2002 | Von Schuckmann |
| 6,427,688 B1 | 8/2002 | Ligotke et al. |
| 6,443,152 B1 | 9/2002 | Lockhart et al. |
| 6,443,307 B1 | 9/2002 | Burridge |
| 6,550,477 B1 | 4/2003 | Casper et al. |
| 6,595,203 B1 | 7/2003 | Bird |
| 6,595,210 B2 | 7/2003 | Ohki et al. |
| 6,655,381 B2 | 12/2003 | Keane et al. |
| 6,681,768 B2 | 1/2004 | Haaije de Boer et al. |
| 6,748,947 B2 | 6/2004 | Keane et al. |
| 6,810,872 B1 | 11/2004 | Ohki et al. |
| 6,871,646 B2 | 3/2005 | Keane et al. |
| 6,932,082 B2 | 8/2005 | Stein |
| 6,941,947 B2 | 9/2005 | Young et al. |
| 6,971,384 B2 | 12/2005 | Gieschen et al. |
| 7,025,056 B2 | 4/2006 | Eason et al. |
| 7,025,057 B2 | 4/2006 | Chawla |
| 7,143,765 B2 | 12/2006 | Asking et al. |
| 7,401,713 B2 | 7/2008 | Ede et al. |
| 7,617,822 B2 | 11/2009 | De Boer et al. |
| 8,109,267 B2 | 2/2012 | Villax et al. |
| 8,631,941 B2* | 1/2014 | Fazzolari ............... A45D 34/04 206/528 |
| 2001/0027790 A1 | 10/2001 | Gieschen et al. |
| 2001/0029948 A1 | 10/2001 | Ingle et al. |
| 2002/0006316 A1 | 1/2002 | Schuler et al. |
| 2002/0020408 A1 | 2/2002 | Knauer |
| 2002/0092523 A1 | 7/2002 | Connelly et al. |
| 2002/0170560 A1 | 11/2002 | Young et al. |
| 2003/0034271 A1 | 2/2003 | Burridge |
| 2004/0107963 A1 | 6/2004 | Finlay et al. |
| 2004/0182387 A1 | 9/2004 | Steiner et al. |
| 2004/0206350 A1 | 10/2004 | Alston et al. |
| 2004/0211419 A1 | 10/2004 | Eason et al. |
| 2004/0236282 A1 | 11/2004 | Braithwaite |
| 2005/0022813 A1 | 2/2005 | Alston |
| 2005/0188988 A1 | 9/2005 | Poole et al. |
| 2006/0005833 A1 | 1/2006 | Gieschen et al. |
| 2006/0108877 A1 | 5/2006 | Tegel |
| 2006/0169278 A1 | 8/2006 | Djupesland et al. |
| 2007/0023381 A1 | 2/2007 | Cerveny |
| 2007/0074721 A1 | 4/2007 | Harmer et al. |
| 2007/0151562 A1 | 7/2007 | Jones et al. |
| 2008/0127970 A1* | 6/2008 | Steiner ............... A61M 15/0028 128/203.14 |
| 2008/0190425 A1* | 8/2008 | Steiner ............... A61M 15/0028 128/203.15 |
| 2008/0251072 A1 | 10/2008 | Lulla et al. |
| 2008/0314384 A1 | 12/2008 | Harris et al. |
| 2009/0250057 A1 | 10/2009 | Wachtel et al. |
| 2009/0308392 A1 | 12/2009 | Smutney et al. |
| 2009/0320838 A1* | 12/2009 | Malhotra et al. ........ 128/203.15 |
| 2009/0321295 A1 | 12/2009 | Ede et al. |
| 2010/0000531 A1* | 1/2010 | Smith et al. ............. 128/203.15 |

FOREIGN PATENT DOCUMENTS

| | | |
|---|---|---|
| EP | 1844809 A1 | 10/2007 |
| GB | 1211168 A | 11/1967 |
| GB | 2179260 A | 3/1987 |
| GB | 2375310 A | 11/2002 |
| GB | 2405798 A | 3/2005 |
| GB | 2420982 A | 6/2006 |
| JP | 08-103499 A | 4/1996 |
| WO | WO 90/07351 A1 | 7/1990 |
| WO | WO 96/09085 | 3/1996 |
| WO | WO 99/06092 A1 | 2/1999 |
| WO | WO 01/05675 A1 | 1/2001 |
| WO | WO 01/26720 A1 | 4/2001 |
| WO | WO 01/56640 A1 | 9/2001 |
| WO | WO 01/85097 | 11/2001 |
| WO | WO 02/098495 A1 | 12/2002 |
| WO | WO 03/000326 A1 | 1/2003 |
| WO | WO 03/015857 A1 | 2/2003 |
| WO | WO 2004/103446 A1 | 12/2004 |
| WO | WO 2005/002654 A3 | 1/2005 |
| WO | WO 2005/025656 A1 | 3/2005 |
| WO | WO 2005/030305 A1 | 4/2005 |
| WO | WO 2006/066910 A1 | 6/2006 |
| WO | WO 2007/007110 A1 | 1/2007 |
| WO | WO 2009/092650 | 7/2009 |

OTHER PUBLICATIONS

International Preliminary Report on Patentability from related International Application No. PCT/US2010/000090 dated Jul. 19, 2011.

* cited by examiner

DELIVERY DEVICE AND RELATED METHODS

This application claims the benefit of U.S. Provisional Application No. 61/641,993, filed May 3, 2012, which is hereby incorporated by reference in its entirety.

BACKGROUND

Medicament in the form of dry powder may be delivered directly into the lungs, such as by inhalation. Administering medicament in this manner may prove less invasive than other drug delivery techniques, such as hypodermic injections. Direct inhalation of medicament may also allow smaller doses to be used to achieve results similar to those of the same drug taken orally. Inhalation may also help avoid undesirable side effects associated with administering drugs orally or by injection.

SUMMARY OF INVENTION

Aspects of the invention relate to devices, systems, and methods that are used to deliver a dose of a powder, such as a medicament, a flavorant, or another substance. The devices, systems and methods may include features that allow the dose to be protected (e.g., from contamination and/or degradation) prior to use, and to be delivered in a metered manner. For example, in some embodiments, the dose is isolated to a selected volume/dose chamber by a barrier, such as a foil layer around the dose chamber or the entire delivery device that prevents the ingress of contaminants and/or the egress of a dose from dose chamber prior to use. As a result, the initial location of the drug dose is known, and the dose may be delivered from the dose chamber in a consistent and predictable way.

In one aspect of the invention, a dose delivery device includes a mouthpiece having an inlet and an outlet, a dose to be delivered to a subject via the mouthpiece and a housing surrounding the mouthpiece and the dose. The mouthpiece and a portion of the housing may be movable relative to each other to form an opening in the housing and/or to extend the mouthpiece from the housing for delivery of the dose. The mouthpiece and housing may be arranged so that the mouthpiece remains attached to the housing after the opening is formed and the mouthpiece is extended from the housing. For example, the housing may be arranged so that a portion of housing at least partially surrounds the dose chamber after the opening is formed and the mouthpiece is extended from the housing. The housing may include a layer of barrier material that interacts with the mouthpiece to form the opening, e.g., the mouthpiece and barrier material may be moved relative to each other so that the barrier material is pierced. The dose chamber may be formed by a portion of the housing, a portion of the mouthpiece, and/or by any other suitable component of the delivery device. Also, the dose chamber may be enclosed by the housing, and the dose chamber may be open to other spaces in the housing, or may be closed relative to other spaces enclosed by the housing. The mouthpiece may be rotatably movable relative to the housing so as to form an opening in the housing and/or open the dose chamber.

In another aspect of the invention, a dose delivery device includes a mouthpiece having an inlet and an outlet, a dose chamber holding a dose to be delivered to a subject via the mouthpiece, where the dose chamber defines a closed first space, and a housing surrounding the mouthpiece and the dose chamber, where the housing defines a closed second space. Movement of a part in the second space (such as a mouthpiece, lever or other component) relative to the housing may form an opening in the housing and/or open the dose chamber to release the dose. The closed first space of the dose chamber may be located within the closed second space, may be coincident with the second closed space, or may be separate from the closed second space. Thus, the housing may define all or part of the dose chamber.

The mouthpiece and a portion of the housing may be movable relative to each other to form an opening in the housing and/or to extend the mouthpiece from the housing for delivery of the dose. Also, the mouthpiece and housing may be arranged so that the mouthpiece remains attached to the housing after the opening is formed and the mouthpiece is extended from the housing. (The mouthpiece and housing may be attached by bonding, mechanical fasteners, or other physical connection, or by having a part of the housing at least partially surround a portion of the mouthpiece or another part to which the mouthpiece is connected. For example, a foil layer that encloses another part of the housing to which the mouthpiece is connected may serve to attach the foil layer and other housing portions to the mouthpiece.) For example, the housing may be arranged so that a portion of housing at least partially surrounds the dose chamber after the opening is formed and the mouthpiece is extended from the housing. The housing may include a layer of barrier material that interacts with the mouthpiece to form the opening, e.g., the mouthpiece and barrier material may be moved relative to each other so that the barrier material is pierced. The dose chamber may be formed by a portion of the housing, a portion of the mouthpiece, and/or by any other suitable component of the delivery device. Also, the dose chamber may be enclosed by the housing, and the dose chamber may be open to other spaces in the housing, or may be closed relative to other spaces enclosed by the housing. The mouthpiece may be rotatably movable relative to the housing so as to form an opening in the housing and/or open the dose chamber.

In another aspect of the invention, a dose delivery device includes a housing defining a closed first space, a mouthpiece having an inlet and an outlet, where the mouthpiece is received in the closed first space defined by the housing, and a dose chamber holding a dose to be delivered to a subject via the mouthpiece. The dose chamber may be located in the closed first space of the housing and define a closed second space in which the dose is held. The mouthpiece may be movable relative to the housing to position the mouthpiece outlet outside of the first space and to open the dose chamber to release the dose. In one embodiment, a removable portion of the housing may be attached to the mouthpiece and be removable from a remainder of the housing so that removal of the removable portion from the remainder of the housing moves the mouthpiece relative to the remainder of the housing. For example, tearing of one portion of the housing from another portion (such as removal of a housing lid) may cause the mouthpiece to move relative to the housing. The mouthpiece may be rotatably and/or linearly movable relative to the housing. In other embodiments, a portion of a housing may be removed from another portion of the housing, such as by tearing, and the mouthpiece subsequently moved relative to the remaining housing portion.

In another aspect of the invention, a dose delivery device includes a housing defining a closed first space, a dose chamber holding a dose to be delivered to a subject, where the dose chamber is located in the closed first space of the housing and defines a closed second space in which the dose is held, a first component located in the closed first space, and a second component that is located in the closed first space and is rotatably attached to the first component. Rotation of the first component (such as a mouthpiece or lever) relative to the second component (such as a housing base or other housing portion) may form an opening in the housing and/or open the dose chamber. In one embodiment, the first component includes an elongated member that extends along an axis, and the first component is rotatably movable relative to the second component about a rotation axis that is transverse (e.g., perpendicular) to the axis. For example, the first component may include a mouthpiece having an inlet at a first end, an outlet at a second end, and a mouthpiece air path extending between the inlet and the outlet. The mouthpiece air path may extend along an outlet axis near the mouthpiece outlet, and the mouthpiece may be rotatably movable relative to the second component about a rotation axis that is transverse (e.g., perpendicular) to the outlet axis. (By "transverse", it is meant that the rotation axis may be at any suitable angle relative to the outlet axis, e.g., between 10 and 90 degrees.)

In another aspect of the invention, a dose delivery device includes a mouthpiece having an inlet, an outlet, and a mouthpiece air path extending between the inlet and the outlet with the mouthpiece air path extending along an outlet axis near the mouthpiece outlet, a base attached to the mouthpiece for rotational movement of the mouthpiece relative to the base about a rotation axis that is transverse to the outlet axis, and a dose chamber holding a dose to be delivered to a subject via the mouthpiece. Rotation of the mouthpiece relative to the base about the rotation axis may open the dose chamber to release the dose.

Aspects of the invention can be used in any suitable arrangement, including dose delivery device that are usable a single time with a single dose chamber, and including a dose delivery device that is usable multiple times with multiple dose chambers. For example, dose delivery device may include a plurality of dose chambers arranged in a multi-dose chamber configuration in which each dose chamber can be serially opened (or two or more dose chambers may be opened simultaneously) and used to deliver a dose to a user.

Among other features, aspects of the invention may provide user convenience in opening and/or using a dose delivery device, provide consistent and controlled opening of a dose chamber and/or housing, provide consistent and effective dose delivery, provide improved manufacturability and/or device tracking (e.g., for distribution control), and others. Other aspects, features and advantages will be apparent from the description of the following embodiments and from the claims.

BRIEF DESCRIPTION OF THE DRAWINGS

Illustrative embodiments of the invention are more particularly described in the following detailed description, taken in conjunction with the accompanying drawings. In the drawings, like reference characters generally refer to the same parts throughout the different views. Also, the drawings are not necessarily to scale, emphasis instead generally being placed upon illustrating principles of the invention.

DETAILED DESCRIPTION

In at least some embodiments, delivery devices described herein include one or more dose chambers for storing and delivering a dose of a substance, such as a powdered medicament, including blended formulations, excipient formulations, neat formulations or combinations thereof, or flavorant, to a subject. The dose chamber may be placed in fluid communication with an air pathway to ready the dose for delivery to the subject. Air may be drawn or pushed through the air pathway so that at least a portion of the air enters the dose chamber to entrain the dose. Air may then exit the dose chamber, laden with powder from the dose chamber, and move toward an outlet of the delivery device to a subject.

According to some aspects, a dose delivery device may include a housing surrounding a mouthpiece and a dose to be delivered to a subject. For example, a mouthpiece may be contained inside of a housing with a removable or piercable foil lid, and the mouthpiece and a portion of the housing may be movable relative to each other to form an opening in the housing so that the mouthpiece can extend from the housing for delivery of the dose. Thus, in one aspect of the invention, a dose delivery device may be arranged so that a mouthpiece and a portion of the housing are movable relative to each other to form an opening in the housing and to extend the mouthpiece from the housing for delivery of the dose. Such an arrangement may make use of the device relatively simple, e.g., a user may both open the housing and expose a mouthpiece contained in the housing in a single operation. This may allow a user to avoid a step of opening a separate external package prior to opening the device housing, e.g., because the external package may not be necessary or desirable.

Figure 1:
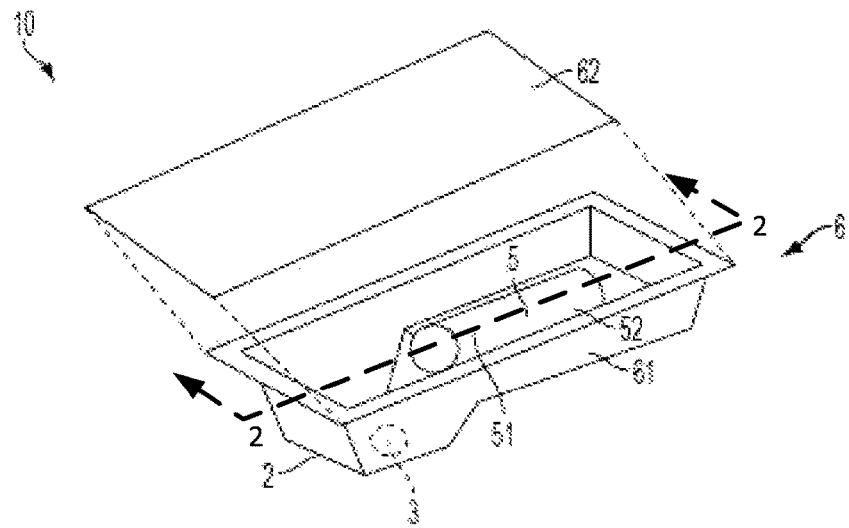
FIG. 1 shows a perspective view of an illustrative dose delivery device.
Figure 2:
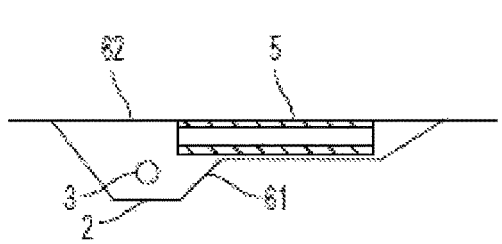
FIG. 2 shows a cross sectional side view of the FIG. 1 embodiment with the mouthpiece located in the housing.

In one illustrative embodiment shown in FIGS. 1 and 2, the dose delivery device 10 includes a housing 6 that encloses a mouthpiece 5 and a dose 3. The housing 6 in this embodiment includes a base 61 (e.g., formed of a molded thermoplastic material) and a lid 62 (e.g., formed of a foil barrier layer material joined to the base 61), but other arrangements are possible. For example, the base 61 and lid 62 could both be made of a layer of barrier material that are joined together, could both be made of a molded plastic material or suitable laminate, made of a combination of molded plastic and a layer of barrier material, and/or take other forms. The dose 3 is located in a dose chamber 2 that in this example is formed by a portion of the base 61. However, as will be made clear in other embodiments discussed herein, the dose chamber 2 may be formed in other ways, such as by one or more portions of the mouthpiece 5, or other components. Also, while the dose chamber 2 in this embodiment is open to other spaces inside the housing 6, the dose chamber 2 may be a closed space inside of the housing, i.e., the dose chamber 2 may be separated from other enclosed space(s) in the housing 6. Providing the dose 3 in a separate dose chamber 2 may help keep the dose 3 in a known and controlled location in the housing 6 and may help with delivery of the dose to a subject. Also, the mouthpiece 5 or other portion of the device 10 may include a valve that helps keep the dose in a desired location (such as in the dose chamber 2) until a suitable time. For example, the mouthpiece 5 may include a duckbill or pinch valve, a film that can be ruptured (e.g., at the start of use of the device 10), a flapper or other arrangement that inhibits dose from passing into the mouthpiece 5 until the user begins flow in the mouthpiece 5 or otherwise causes the valve or other structure to open.

Figure 3:
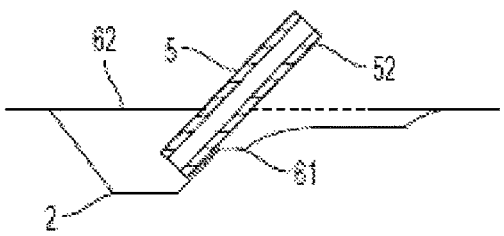
FIG. 3 shows a cross sectional side view of the FIG. 1 embodiment with the mouthpiece outlet extended from an opening in the housing.

FIG. 3 shows a side view of the device 10 in a condition where the mouthpiece and at least a portion of the housing 6 have been moved relative to each other so that an outlet of the mouthpiece extends from the housing 6. Prior to such movement, the mouthpiece 5 may be maintained inside the housing 6, e.g., to keep the mouthpiece 5 sterile or otherwise in a desired condition. A variety of different techniques may be used to move the mouthpiece 5 to the condition shown in FIG. 3. For example, in this embodiment, a user may press upwardly on a portion of the base 61 that is positioned below the mouthpiece 5 so that the base 61 is at least partially deformed and the mouthpiece 5 pierces the lid 62 to form an opening in the housing 6. In some embodiments, the mouthpiece 5 may include a force concentrator, such as one or more spikes, knife edges, tabs, etc., that help to pierce the lid 62 and form the opening in the housing 6. The mouthpiece 5 may be moved through the opening so that the outlet 52 of the mouthpiece 5 is positioned outside of the housing 6. A user may then interface with the outlet 52, e.g., by placing the outlet 52 into communication with a mouth or nose and/or placing an extension tube or other device on the mouthpiece 5 to conduct dose to the user. The mouthpiece 5 may be attached to a part of the housing 6, such as a portion of the base 61 near a midpoint of the mouthpiece 5, so that the mouthpiece 5 and the housing 6 remain attached even after the mouthpiece 5 is extended from the housing 6. This may make the device 10 more convenient for a user, e.g., by keeping all or most of the parts of the device 10 connected during and after use. Alternately, or in addition, attachment of the mouthpiece 5 to the housing 6 may help guide the motion of the mouthpiece 5, e.g., the attachment of the mouthpiece 5 to the housing 6 may serve as a pivot point that helps guide the mouthpiece 5 to contact a desired portion of the housing 6 during opening and/or locate the mouthpiece in a desired position when the mouthpiece is extended from the housing 6.

In another embodiment, rather than causing the mouthpiece 5 to interact with the housing 6 to form an opening in the housing 6, a portion of the housing 6 may be removed or otherwise acted on to form an opening through which the mouthpiece 5 is extended. For example, the lid 62 may be completely or partially removed from the base 61 (e.g., by peeling the lid 62 back) to expose the outlet 52 end of the mouthpiece 5. Thereafter, the mouthpiece 5 may be moved to position the outlet 52 outside of the housing 6, e.g., by a user grasping the exposed mouthpiece portion and lifting the mouthpiece outlet end from the housing 6.

With the mouthpiece outlet 52 exposed, the dose delivery device 10 may be used in any suitable way, such as by inhaling to draw air through the dose chamber 2 to entrain the dose 3, which then passes through the mouthpiece to the outlet 52. Air may be introduced into the dose chamber 2 in any suitable way, such as by one or more openings in the housing 6, by channels or other features in the mouthpiece 5, etc. Also, the device 10 may have other features, such as classifier structures to help break down and allow the passage of only suitably sized dose particles, or swirl chambers, screens, flow straightener structures, air bypass features to add air to a flow of entrained dose, and others, as these features are not necessarily required for certain aspects of the invention. For example, air passageways in the delivery device may be configured to accomplish different effects, such as creating swirling air patterns within the dose chamber, which may help to entrain the powdered dose and meter it to the user. In other embodiments, passageways may be sized to control the flow rates and/or volumes through particular portions of the delivery device, e.g., air flow may be at lower mass or volumetric flow rates in the dose chamber than through bypass channels that feed air to the mouthpiece to help meter the release of dose from the dose chamber 2. Also, although the mouthpieces in these illustrative embodiments include a single main air path, a mouthpiece may have two or more air paths, whether for conducting air, air with entrained dose, or other fluid. It should also be understood that aspects of the invention may be used in single use devices, or in multi-use devices, such as a cassette that includes a circular array of dose delivery devices like that shown in FIGS. 1-3 carried on a disk. For example, a disk shaped structure could include several dose delivery devices 10 like that in FIG. 1 along with other suitable structure to move the mouthpiece 5 to form the opening and extend the outlet 52 from the housing 6, e.g., upon a user pressing an actuation button. In another embodiment, multiple devices 10 may be arranged in a strip that may be separated from each other, e.g., by tearing one device 10 from others in the strip at a perforation.

In another aspect of the invention, a dose delivery device includes a mouthpiece having an inlet, an outlet, and a mouthpiece air path extending between the inlet and the outlet. The mouthpiece air path may extend along an outlet axis near the mouthpiece outlet. The device may also include a base attached to the mouthpiece for rotational movement of the mouthpiece relative to the base about a rotation axis that is transverse to the outlet axis. For example, the mouthpiece may include an elongated tube that is rotatable relative to the base about a rotation axis that is perpendicular to a longitudinal axis of the tube. A dose chamber holding a dose may be opened in response to rotation of the mouthpiece relative to the base about the rotation axis.

Figure 4:
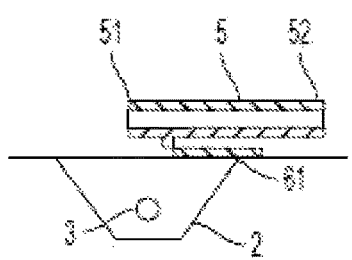
FIG. 4 shows a side view of another embodiment in which a mouthpiece is moveably mounted relative to a dose chamber.
Figure 5:
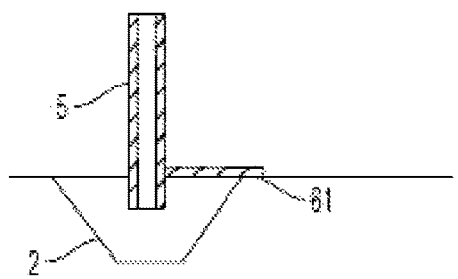
FIG. 5 shows a side view of the FIG. 4 embodiment with the mouthpiece moved to a position in which the dose chamber is opened.

For example, FIGS. 4 and 5 show an illustrative embodiment in which a mouthpiece 5 is attached to a base 61 that may be part of a housing 6. The mouthpiece 5 may be pivoted relative to the base 61 about a rotation axis that is perpendicular to an outlet axis along which air may flow near the mouthpiece outlet 52. (Although in this embodiment, the mouthpiece 5 includes a linear flow path from the inlet 51 to the outlet 52, the mouthpiece 5 may have a flow path with one or more turns, bends or other arrangements. Thus, the flow path at the outlet 52 need not necessarily be collinear or parallel with the flow path at the inlet 51 or other portions of the mouthpiece 5.) In this embodiment, the mouthpiece 5 is attached to the base 61 by a living hinge, but other connection arrangements are possible, such as a standard hinge structure having a hinge pin, a cam slot and pin, a ball and socket joint, and others. In this embodiment, the housing 6 includes a layer of barrier material (e.g., metal foil) positioned so that an inlet end 51 of the mouthpiece 5 pierces the barrier material when the mouthpiece 5 is moved to a position shown in FIG. 5. This forms an opening in the dose chamber 2, allowing a dose 3 in the chamber 2 to be introduced into air flow in the mouthpiece 5. However, other arrangements are possible, such as a portion of the housing 6 having a perforated, scored or otherwise weakened portion (e.g., like that in a common soda can) that opens when pushed downwardly by the inlet end 51 of the mouthpiece 5. While in this embodiment, the housing 6 forms an enclosed space that is coincident with the dose chamber 2, the device 10 could be arranged in other ways, e.g., so that the housing 6 defines one space that encloses the mouthpiece 5 and another space that defines the dose chamber 2. For example, another housing portion may be provided that encloses the mouthpiece 5, e.g., to prevent contamination of the mouthpiece or unintended movement of the mouthpiece to open the dose chamber 2.

Figure 6:
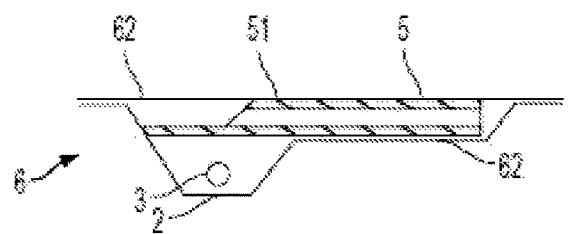
FIG. 6 shows a side view of another embodiment in which a mouthpiece may be moved from within the housing to open a dose chamber.
Figure 7:
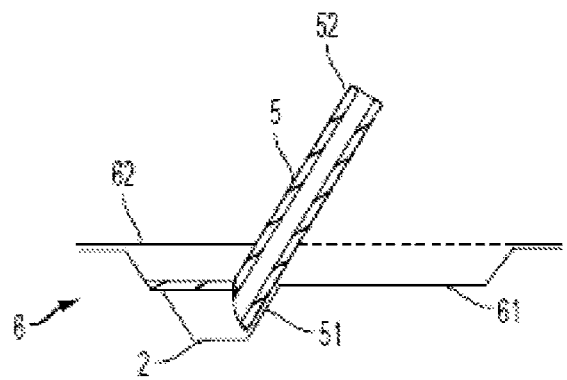
FIG. 7 shows a side view of the FIG. 6 embodiment with the mouthpiece outlet extended from an opening in the housing.
Figure 8:
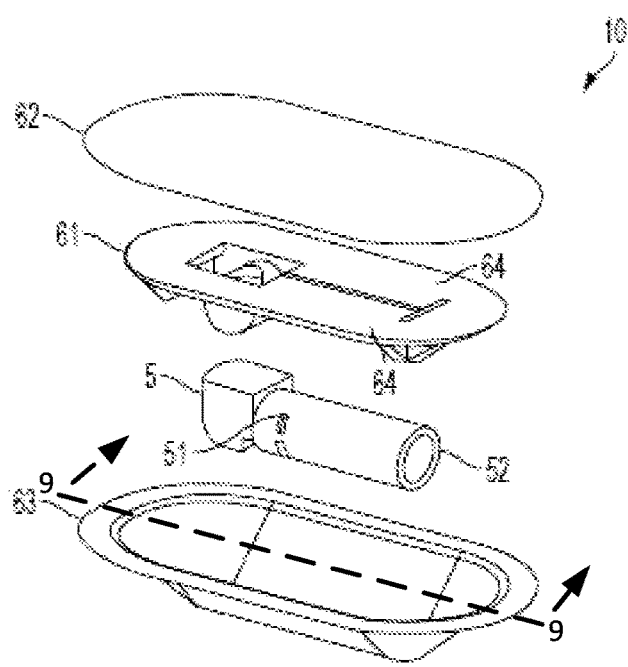
FIG. 8 shows an exploded view of yet another illustrative embodiment in which the housing includes an opening mechanism in the form of doors that move to form an opening in the housing.

FIGS. 6 and 7 show another embodiment in which movement of a mouthpiece opens a dose chamber, as well as forms an opening in a housing from which the outlet of the mouthpiece may be extended. This embodiment is similar to that in FIGS. 1-3, except that an inlet end 51 of the mouthpiece 5 is arranged so as to form an opening into the dose chamber 2 when the mouthpiece 5 is moved to the position shown in FIG. 7. For example, the inlet end 51 of the mouthpiece 5 may include a perforated, scored or otherwise weakened line so that when the mouthpiece 5 is moved relative to the housing 6, the perforated section breaks to open the dose chamber 2 and allow the inlet end 51 to move into the dose chamber 2. In another embodiment, the dose chamber 2 may be closed by a layer of barrier material, such as a foil, that is pierced by the inlet end 51 of the mouthpiece 5 as the mouthpiece is moved to the position in FIG. 7. As discussed above with respect to the FIGS. 1-3 embodiment, the outlet 52 of the mouthpiece 5 may be extended from the housing 6 in any suitable way, such as by using the mouthpiece 5 to pierce a lid 62 to form an opening, by removing the lid 62 or a portion of the lid 62 prior to moving the outlet 52 out of the housing 6, or others.

Figure 9:
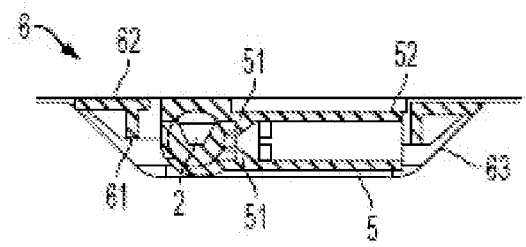
FIG. 9 shows a side view of the FIG. 8 embodiment with the mouthpiece located in the housing.
Figure 10:
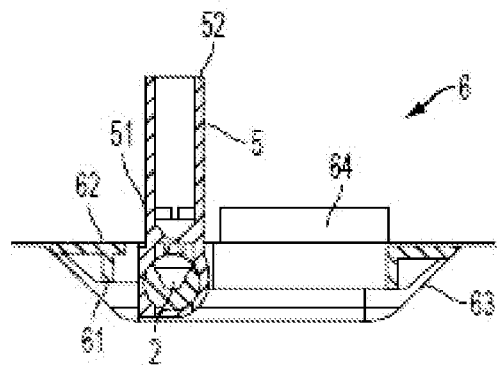
FIG. 10 shows a side view of the FIG. 8 embodiment with the mouthpiece outlet extended from an opening in the housing.
Figure 11:
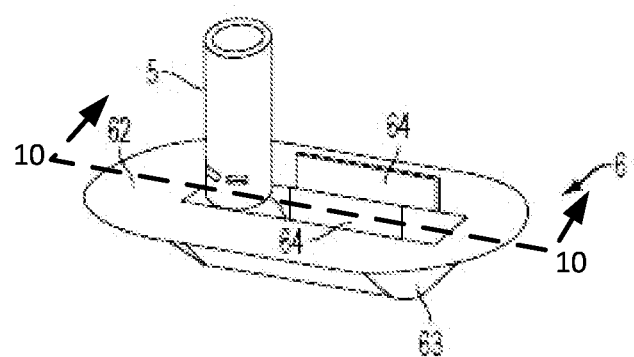
FIG. 11 shows a perspective view of the FIG. 8 embodiment in the condition of FIG. 10.

In another aspect of the invention, a dose delivery device may include a housing surrounding the mouthpiece and the dose chamber, and movement of a part inside the housing relative to the housing may form an opening in the housing, e.g., through which a mouthpiece may be extended. For example, movement of the mouthpiece or another element in the housing may form an opening in the housing through which the mouthpiece may extend. FIGS. 8-11 show an embodiment in which one or more doors may be moved to form an opening in a housing through which a mouthpiece may extend. In this illustrative embodiment, the housing 6 includes a lid 62 and a tray 63 that enclose a base 61 and a mouthpiece 5. The lid 62 and tray 63 may be formed of a layer of barrier material (such as a foil) and the base 61 may be molded of a plastic material, but other arrangements are possible. For example, the base 61 and tray 63 may be made as a single unitary structure. As can be seen in FIG. 9, portions of the mouthpiece 5 and the base 61 cooperate to form a dose chamber 2 in which a dose 3 is retained until the dose chamber 2 is opened. The base 61 includes a pair of doors 64 or other opening mechanism that are arranged to pivot upwardly to form an opening in the housing 6 as shown in FIGS. 10 and 11. That is, in this embodiment, the doors 64 may be moved to pierce the lid 62 and swing upwardly and away from the mouthpiece 5 to form an opening through which the mouthpiece 5 may be extended. In some embodiments, such as where the mouthpiece 5 is made of a relatively soft or flexible material, the mouthpiece 5 may not be easily used to itself contact and pierce a lid 62 or other housing portion to form an opening, or such a mouthpiece 5 may not be capable of piercing the housing in a consistent and controlled way. Thus, an opening mechanism, such as one or more doors 64 or other structures, may be used to contact the lid 62 to form an opening. The doors 64 may include a force concentrating feature, such as one or more spikes, knife edges, or other, that can concentrate force on a particular area of the lid 62 so as to form an initial opening from which the lid 62 may be more easily torn to form an opening. In addition, or alternately, the doors 64 or other opening mechanism may be used to define the shape, size or other features of the opening formed in the housing. For example, it may be important in some embodiments to ensure that the housing opening is formed so that portions of the housing do not interfere with an air inlet to the dose chamber or other portions of the device 10. The doors 64 or other opening mechanism may ensure that portions of the housing 6 are suitably moved to provide desired clearance or other features. In some embodiments, the doors 64 or other opening mechanism may or may not be bonded to the lid 62 or other housing portion at which an opening is formed. In some cases, bonding the doors 64 to the lid 62 may help control movement of the lid 62 during formation of the opening as well as help maintain attachment of the lid 62 to other housing portions. In other cases, it may be desirable to have the doors 64 or other opening mechanism be free of direct connection to the lid 62, e.g., to allow the doors 64 to form an opening a cause the lid to be peeled back without requiring excessive forces.

Although in this embodiment the doors 64 are moved from a closed position (FIG. 9) to an open position (FIGS. 10 and 11) by a user pressing on the tray 63 adjacent a lower side of the mouthpiece 5 so that the mouthpiece 5 pushes the doors 64 through the lid 62 and to the open position, other arrangements are possible. For example, a portion of the lid 62 may be first peeled from the base 61 to expose the doors 64, which are then swung outwardly to expose the mouthpiece 5. In another embodiment, peeling of a portion of the lid 62 may cause the doors 64 to move to the open position, allowing a user to grasp the mouthpiece 5 and extend the outlet 52 of the mouthpiece out of the housing 6. In another arrangement, a pull tab may be connected to the outlet end 52 of the mouthpiece 5 pulled upwardly by a user so as to pull the mouthpiece 5 through the door 64 opening and the lid 62.

The device 10 may be arranged so that when the mouthpiece 5 is extended from the housing opening, an audible and/or tactile "click", contact of the mouthpiece with a hard stop, or other indication is provided to the user to indicate that the mouthpiece 5 has reached a fully extended position. This position may ensure that the mouthpiece 5 is properly aligned with the dose chamber 2 or other portion of the device 10, that the dose chamber 2 is fully opened, or other conditions exist for proper use of the device 10. The mouthpiece 5 may lock in the extended position, e.g., to prevent positioning the mouthpiece 5 in the housing 6 again and reuse of the device.

Another aspect of the invention included in the FIGS. 8-11 embodiment is that rotation of a pair of components relative to each other may form an opening in a housing and/or open a dose chamber. In this illustrative embodiment, the mouthpiece 5 is rotatably mounted to the base 61 so that when the mouthpiece 5 is moved to the position shown in FIGS. 10 and 11, the dose chamber 2 is opened and the dose 3 released for entrainment into an air flow in the mouthpiece 5. That is, in this embodiment, a portion of the base 61 forms a cavity in which the dose is held. A portion of the mouthpiece 5 covers the cavity when the mouthpiece 5 is in the position shown in FIG. 9, closing the dose chamber 2 and retaining the dose 3. However, when the mouthpiece is moved to at least partially extend from the housing 6 as shown in FIG. 10, the mouthpiece 5 rotates relative to the base 61 so that the cavity is exposed to the inlet end 51 of the mouthpiece 5. Although not shown, movement of the mouthpiece 5 to the position in FIG. 10 also opens air pathway(s) into the dose chamber 2 so that as air is withdrawn from the outlet 52 of the mouthpiece 5, air may enter the dose chamber 2 to entrain dose and pass to the inlet 51.

Figure 12:
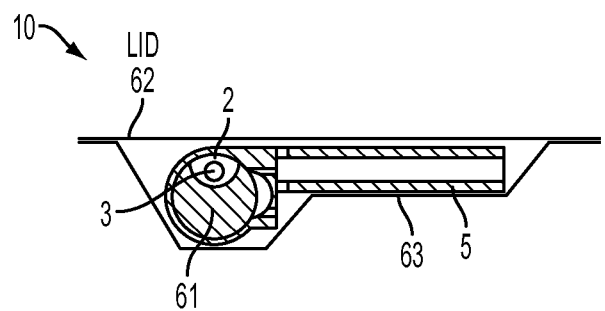
FIG. 12 shows yet another embodiment of a dose delivery device in which a mouthpiece is rotatably mounted to a housing and helps form a dose chamber.
Figure 13:
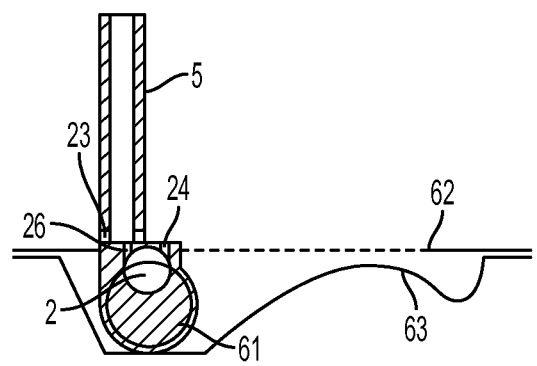
FIG. 13 shows the FIG. 12 embodiment with the mouthpiece extended from an opening in the housing.

FIGS. 12 and 13 show another embodiment that is similar to that of FIGS. 8-11 in that movement of the mouthpiece 5 can serve to open a dose chamber. However, the embodiment of FIGS. 12 and 13 does not include the doors 64 of FIGS. 8-11, and instead the mouthpiece 5 may itself form an opening in the housing 6, or may be moved through an opening in the housing 6 formed in another way, such as by removing a lid 62 of the housing 6. FIGS. 12 and 13 also show a dose chamber air inlet passageway 24 through which air may enter the dose chamber 2, an air outlet passageway 26 through which air and entrained dose 3 may pass to the inlet 51, and one or more bypass openings 23 through which air may enter the inlet 51. The size and configuration of the passageways 24 and 26 and the bypass openings 23 may be sized or otherwise arranged to meter the rate at which dose is entrained into the air flow in the mouthpiece and/or otherwise influence flow characteristics of the device. Similar arrangements (whether in form or concept) may be used in other device embodiments described herein.

Figure 14:
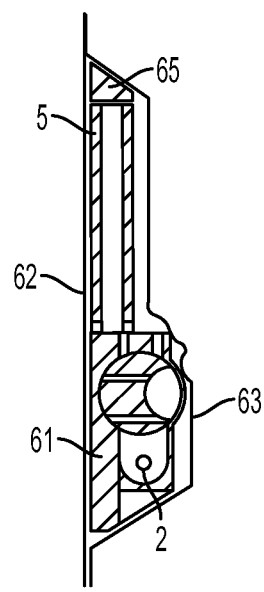
FIG. 14 shows yet another embodiment of a dose delivery device in which a lever is rotatably mounted to a housing and helps form a dose chamber.
Figure 15:
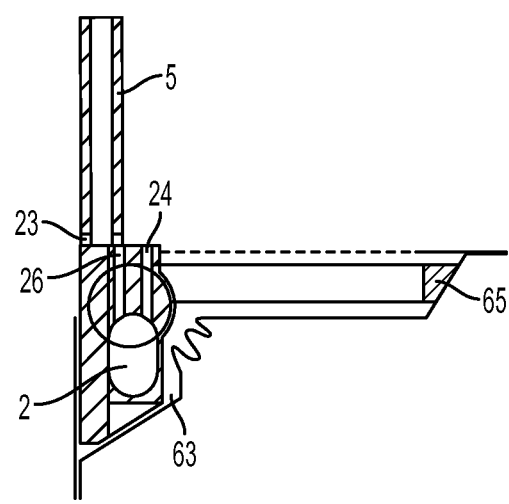
FIG. 15 shows the FIG. 14 embodiment with the lever rotated to open a dose chamber and expose a mouthpiece outlet.

In accordance with another aspect of the invention, a dose delivery device may accommodate relative movement of first and second components at least partially contained in a housing to form an opening in the housing and/or open a dose chamber. Thus, a mouthpiece need not necessarily be manipulated by a user to form an opening in the housing and/or open a dose chamber. Instead, another component in the housing may be moved to form an opening in the housing and/or open a dose chamber. For example, FIGS. 14 and 15 show an embodiment in which a mouthpiece 5 is fixed to a base 61 of the housing 6, which also includes a lid 62 and tray 63 that enclose the mouthpiece 5 and base 61. As discussed above, the lid 62 and tray 63 may include a layer of barrier material or other suitable material to allow the housing 6 to be opened. A lever 65 is rotatably mounted to the base 61 and cooperates with the base 61 to form a dose chamber 2 that is initially closed in FIG. 14. However, when the lever 65 is rotated to the position shown in FIG. 15, the dose chamber 2 is opened and the dose 3 released for entrainment. Movement of the lever 65 may pierce the lid 62 (e.g., by forcing the lid 62 into contact with the mouthpiece 5, causing the lid 62 to rupture) to form an opening in the housing 6. Other portions of the lid 52 and tray 63 may remain attached to the lever 65 and/or the base 61 so as to keep all or most parts of the device 10 attached together after use. Thus, a portion of the housing 6 may at least partially enclose or surround the base 61, the dose chamber 2 and/or other portions of the device 10 after an opening is formed in the housing 6 and the mouthpiece outlet 52 extended from the opening.

Another possible advantage of having components of the device 10 remain attached together after use may be to allow tracking of components of the device 10 both before and after use. That is, since the device 10 may be arranged to keep its parts attached together throughout the life of the device 10, the device 10 may be arranged to carry information that can identify one or more of the device components so that the information can be used to determine characteristics of those components. For example, the device 10 could carry indicia, whether in the form of printed alphanumeric text, a barcode, an encoded magnetic strip, an RFID tag or other data element, a computer chip, etc., that can be used to identify one or more components of the device. The indicia may be used to determine when the device was made, what type and/or amount of dose is contained in the device, an intended user and/or use of the device, intended countries or other jurisdictions in which the device is authorized or otherwise available for use, and other. Indicia can also be used to track/encourage compliance with taking the medication. Thus, the indicia could be read from the device 10 (e.g., using a suitable RFID interrogator or reader) and used to determine the desired information. The indicia could include the desired information, such as the manufacture date, or could be used to retrieve such information from another source, such as a database associated with a suitable Internet website. The indicia may be located inside of the housing 6, or on an exterior of the housing 6, and may be useable with any suitable technology, such as a cell phone camera, associated image processing software and database access to image a 2D code, decode the image and access a suitable database to retrieve desired information.

Figure 16:
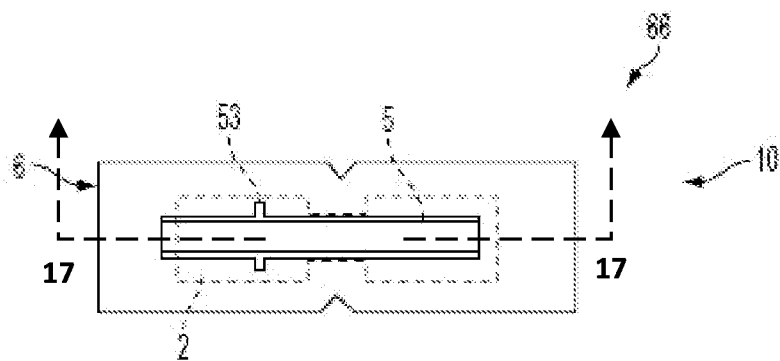
FIG. 16 shows a top view of yet another embodiment in which a mouthpiece is slidably movable relative to a housing portion at a dose chamber.
Figure 17:
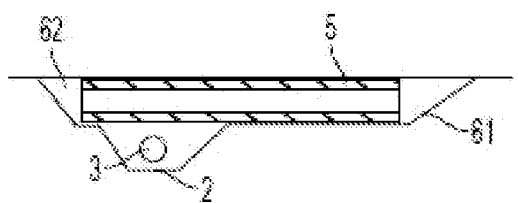
FIG. 17 shows a side view of the FIG. 16 embodiment.
Figure 18:
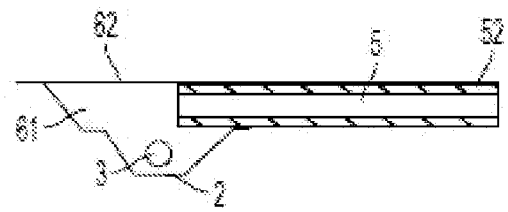
FIG. 18 shows a side view of the FIG. 16 embodiment with the mouthpiece outlet exposed from an opening in the housing and moved to open the dose chamber.

FIGS. 16-18 show another embodiment of a dose delivery device 10 in which movement of a part in the housing 6 may open a dose chamber 2. In this illustrative embodiment, a mouthpiece 5 is slidably moveable in a housing 6 once an opening is formed in the housing 6 through which the outlet 52 of the mouthpiece 5 may be extended. As shown in FIG. 16, the mouthpiece 5 has tabs 53 that control a limit to which the mouthpiece 5 may move to the right relative to the dose chamber 2. In this embodiment, a user may grasp the outlet end 52 of the mouthpiece 5 and pull the mouthpiece 5 toward the right relative to the dose chamber 2. This movement may form an opening in the housing 6, e.g., by causing the housing 6 to separate into two parts at a break line 66. The break line 66 may be formed by a perforation, scoring, notches or other features that cause the housing 6 to separate into two parts or otherwise form an opening when the mouthpiece 5 is moved relative to the portion of the housing at the dose chamber 2. In an alternate embodiment, movement of the mouthpiece 5 may cause a portion of the mouthpiece 5 to pierce the housing 6 to form an opening through which the outlet 52 may extend. Movement of the mouthpiece 5 to the position shown in FIG. 18 may cause the dose chamber 2 to be opened to release the dose 3 for entrainment. That is, the mouthpiece 5 may close the dose chamber 2 when in the position shown in FIG. 17, but open the dose chamber 2 when moved to the position shown in FIG. 18. For example, the inlet end 51 of the mouthpiece 5 may tear a barrier layer (not shown) as the mouthpiece 5 is moved to open the dose chamber 2. The tabs 53 on the mouthpiece 5 may limit the range of movement of the mouthpiece 5, e.g., preventing the mouthpiece 5 from being completely removed from the portion of the housing 6 at the dose chamber 2. Movement of the mouthpiece 5 may also form other openings in the housing 6, e.g., for a dose chamber inlet passageway 24 or bypass opening 23.

A barrier provided by the housing 6 or other components for a dose chamber 2 or other enclosed spaces may be formed of various materials. According to some embodiments, a layer of barrier material may include an aluminum foil that is substantially impervious to light and moisture, although in other embodiments, barriers may be permeable to some degree of moisture and light. The barrier may be readily adhered to other barriers, such as for foil-on-foil embodiments, or to other structures of a delivery device, that may be formed of plastic. Adhesives, heat weld, friction welds, and other fastening techniques may be used to affix barriers and to provide a seal between the barrier and mating structure.

It is to be appreciated that although various embodiments of the delivery devices are discussed and illustrated herein as a single dose device, that a plurality of any of the dose chambers may be incorporated into a device that may deliver multiple doses. Incorporating multiple dose chambers into a common device may allow some features of a delivery device to be shared among different dose chambers. By way of example, a multi-dose device may include a common outlet that is used to deliver, sequentially, doses from each of the dose chambers to a subject, when needed. Other features may be shared among the different dose chambers of a common, multi-dose device, such as a single actuation button and/or punch that is moved sequentially into registration with each dose chamber to move an opening mechanism between a first and second position to ready a dose for delivery, or a cassette is moved into registration with the punch. Additionally or alternatively, a multi-dose configuration may reduce the overall cost per dose to be delivered from a delivery device.

It is to be appreciated that the embodiments illustrated herein are merely representative embodiments of the various inventions, and that modifications may be made without departing from the spirit of the invention. By way of example, air pathways may be modified to have different shapes or features, or be located in various different parts of the dose deliver device for manufacturing or other reasons.

In some embodiments, the devices, systems and methods may be free of secondary packaging to facilitate rapid and easy delivery of the drug when the drug needs to be delivered as fast as possible under a stressful circumstance, such as in an emergency situation. However, some embodiments may have the entire device enclosed in a bag, e.g., of barrier layer foil or other material, to help preserve the dose 3 or otherwise provide the dose 3 with suitable conditions for storage.

Embodiments described herein may be configured for passive or active applications, or a combination of passive and active fluid administration. For example, each of the embodiments described herein may include use of a compressed fluid to assist in dispersing the drug.

The devices and systems described herein may be integrated into a wide variety of delivery configurations including, for example, a single-dose and multi-dose applications, in either active, passive, or active/passive applications. In addition, the devices, systems and methods may be applied to combination dose configurations and therapies.

The devices, systems and methods described herein may be used to deliver materials, other than a drug/medicament, to the body. The materials may be delivered through the mouth and/or nose and into the oral cavity, nasal cavity, and/or to the lungs. Materials that are intended to be delivered into the oral cavity include, for example, nutritional compositions (such as sugars, candy, food, vitamins, and quick energy supplements in liquid and/or powder (e.g., nanoparticles) form) and non-nutritional compositions (such as flavorants (e.g., esters)). Other materials that may be delivered into the oral cavity include those used for oral hygiene and dental treatment (e.g., breath fresheners, fluoride treatments, teeth whiteners, antibacterial compositions, mouthwashes). Drugs and related compositions (such as anesthetics, therapeutic markers) may also be delivered into the oral cavity. Materials that the may be inhaled into the lungs include, for example, drugs (e.g., for treating asthma, bronchitis, diabetes, pneumonia) and therapeutic markers (such as dyes, scanning agents, radio labeling or tagging agents, UV labeling agents, contrasts agents in liquid and/or powder (e.g., nanoparticles) form). In this respect, it is to be appreciated that any of the above materials may be used in the devices, systems, and methods described herein in place of drug(s)/medicaments. It is also to be appreciated that the terms "drug" and "medicament" are used interchangeable herein, and include any of the foregoing compositions and any others, whether in powder, liquid or other form, that may be delivered to a human or animal for therapeutic, diagnostic, or other effect. In certain aspects, the delivery device is configured for use with other entranceways into a human or animal body, whether naturally formed or created otherwise, and with aspects of the human or animal body other than the respiratory system. Although the embodiments described incorporate air as the fluid for delivering the medicament, other fluids are contemplated as should be apparent to one of skill in the art.

Although embodiments are described as including a "mouthpiece," it should be understood that a "mouthpiece" as used herein refers to an element that is downstream of a dose chamber and is intended to deliver an air/dose combination toward an ultimate outlet located at or near a user's mouth, nose or other receiving area. Thus, a "mouthpiece" need not necessarily be intended for contact with a human mouth. For example, a mouthpiece may be intended for use near a mouth, such as where a user holds the device spaced from the mouth and inhales dose/air emitted from the device outlet. In this situation (and others) the dose could potentially be delivered by squeezing a flexible dose chamber or other flexible portions of the housing and the resulting compressed air pushes the dose out to the user. In another embodiment, a mouthpiece may be intended for use with another element that is engaged with the mouthpiece (e.g., at the mouthpiece outlet 52) and is intended for contact with the user's mouth. In one example, a disposable or reusable sleeve or other conduit may be connected to the mouthpiece outlet 52 and provide an extension of the air path of the device beyond the mouthpiece outlet 52. The fact that a dose delivery device is used, or intended for use, with such a sleeve would not render the air flow component downstream of the dose chamber (i.e., the "mouthpiece") that conducts an air/dose combination not a "mouthpiece" as used herein.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A dose delivery device, comprising:
a mouthpiece having an inlet and an outlet;
a dose to be delivered to a subject via the mouthpiece; and
a housing surrounding the mouthpiece and the dose such that the mouthpiece is enclosed inside the housing, the housing including a barrier layer, wherein the mouthpiece is movable relative to the housing and arranged to pierce the barrier layer forming an opening through the housing when moved relative to the housing to an opened position such that the mouthpiece extends from inside the housing through the opening to outside the housing for delivery of the dose.

2. The device of claim 1, wherein the mouthpiece and housing are arranged so that the mouthpiece remains attached to the housing after the opening is formed and the mouthpiece is extended through the housing.

3. The device of claim 1, wherein the housing is arranged so that a portion of housing at least partially surrounds the dose chamber after the opening is formed and the mouthpiece is extended through the housing.

4. The device of claim 1, wherein a portion of the housing forms at least a part of a dose chamber that holds the dose.

5. The device of claim 1, wherein the housing includes a base that is attached to the mouthpiece so that the mouthpiece is rotatably movable relative to the base.

6. The device of claim 5, wherein a portion of the base and a portion of the mouthpiece cooperate to form a dose chamber that holds the dose.

7. The device of claim 5, wherein the mouthpiece is attached to the base via a living hinge.

8. The device of claim 1, further comprising a dose chamber that holds the dose in a closed space inside the housing.

9. The device of claim 8, wherein the mouthpiece and the housing are arranged to open the dose chamber in response to movement of the mouthpiece and a portion of the housing relative to each other.

10. A dose delivery device, comprising:
a mouthpiece having an inlet and an outlet;
a dose chamber holding a dose to be delivered to a subject via the mouthpiece, the dose chamber defining a closed first space; and
a housing surrounding the mouthpiece and the dose chamber and including a layer of barrier material, the housing defining a closed second space enclosing the mouthpiece, wherein the mouthpiece is arranged to pierce the barrier material forming an opening in the housing when the mouthpiece is moved relative to the housing to an opened position, which opens the dose chamber to release the dose through the opening.

11. The device of claim 10, wherein the mouthpiece is movable relative to the housing to form the opening in the housing and open the dose chamber.

12. The device of claim 10, wherein the mouthpiece is movable to extend from the housing through the opening.

13. The device of claim 10, wherein a portion of the housing defines at least part of the dose chamber.

14. The device of claim 10, wherein a portion of the mouthpiece defines at least part of the dose chamber.

15. The device of claim 10, wherein the mouthpiece and housing are arranged so that the mouthpiece is extendable from the housing through the opening.

16. The device of claim 15, wherein the housing is arranged so that a portion of housing at least partially surrounds the dose chamber after the opening is formed and the mouthpiece is extended from the housing.

17. The device of claim 10, wherein the housing includes a base that is attached to the mouthpiece so that the mouthpiece is rotatably movable relative to the base.

18. The device of claim 17, wherein a portion of the base and a portion of the mouthpiece cooperate to form the dose chamber.

* * * * *